United States Patent [19]
Theriot

[11] Patent Number: 5,907,063
[45] Date of Patent: May 25, 1999

[54] AROMATIC BROMINATION PROCESS

[75] Inventor: Kevin J. Theriot, Baton Rouge, La.

[73] Assignee: Albemarle Corporation, Richmond, Va.

[21] Appl. No.: 09/046,753

[22] Filed: Mar. 24, 1998

[51] Int. Cl.$^6$ ...................... C07C 209/00; C07C 235/00; C07C 321/00; C07C 43/02
[52] U.S. Cl. ........................... 564/412; 564/218; 568/56; 568/656; 568/779; 568/27
[58] Field of Search ............................ 568/56, 656, 779, 568/27; 564/218, 412

[56] References Cited

PUBLICATIONS

Olah, G.A. et al., *Synthesis,* Synthetic Methods and Reactions: 127. Regioselective para Halogenation of Phenols, Phenol Ethers and Anilines with Halodimethylsulfonium Halides, (10), pp. 868–870 (1986).
Fletcher, T.L. et al., *J. Chem. Soc.,* "Alkylation–Bromination of Fluoreneamines with Alkyl and Aralkyl Bromides in Dimethyl Sulphoxide," pp. 4588–4591 (1965).
Floyd, M.B. et al., *J. Org. Chem.,* "The Oxidation of Acetophenones to Arylglyoxals with Aqueous Hydrobromic Acid in Dimethyl Sulfoxide," vol. 50(25), p. 5026 (1985).
Epstein, W.W. et al., *Chemical Reviews,* "Dimethyl Sulfoxide Oxidations," vol. 67(3), pp. 247–260 (1967).
Fletcher, T.L. et al., *J. of Med. Chem., New Compounds,* "New Thio Derivatives of Carcinogenic Arylamines. IV. 4–Acetamido–3–methylthiodiphenyl," vol. 13(4), p. 78 (1970).
Zoretic, P.A., *J. Org. Chem.,* "Indirect Bromination by Reaction of Aniline Hydrobromide with Dimethyl Sulfoxide," vol. 40(12) pp. 1867–1868 (1975).
Srivastava, S.K. et al., *Chem. Commun.,* "Novel Site–Specific One–Step Bromination of Substituted Benzenes," (23), pp. 2679–2680 (1996).
Majetich et al., *J. Org. Chem.,* "Electrophilic Aromatic Bromination Using Bromodimethylsulfonium Bromide Generated in Situ," vol. 62, pp. 4321–4326 (1997).
Megyeri, G. et al., *Synth. Commun.,* "Halogenation of Indole Alkaloids With Halodimethylsulfonium Halogenids and Halodimethylsulfoxonium Halogenids," vol. 19(20), pp. 3415–3430 (1989).
Singh, B. et al., *Heterocycles,* "An Efficient and Novel Synthesis of Fused Thiazol–(2(3H)–Ones," vol. 36(1) (1993).
Rehse, K. et al., *Arch. Pharm.,* "A New Method for 5,6–Disubstituted 1,2,3,4–Tetrahydro–β–carboline Derivaten," vol. 313(4), pp. 379–381 (1980).

*Primary Examiner*—Alan Siegel
*Attorney, Agent, or Firm*—E. E. Spielman, Jr.

[57] ABSTRACT

Activated aromatic compounds are more economically ring brominated by reacting the compounds with a sulfoxide/HBr brominating agent while removing water from the reaction mixture. The water removal provides high conversions and yields when employing stoichiometric quantities of reactants.

10 Claims, No Drawings

AROMATIC BROMINATION PROCESS

BACKGROUND OF THE INVENTION

This invention relates generally to the bromination of organic compounds and more particularly to an improved process for the ring bromination of activated aromatic compounds under mild conditions (no $Br_2$) using a sulfoxide/HBr brominating agent such as dimethyl sulfoxide/HBr.

The one-step bromination of oxidatively unstable benzene derivatives, such as aniline and phenol, using a dimethyl sulfoxide/HBr brominating agent has been described in the literature. For example, see S. K. Srivastava et al., *J. Chem. Soc. Chem. Comm.*, 1996, 2679–2680 and Majetich et al.,*J. Org. Chem.* 1997, 62, 4321–4326. A large excess of brominating agent is used and especially the dimethyl sulfoxide which is also employed as a solvent for the reaction. Although suitable for academic studies, the use of excess brominating agent would be uneconomical for commercial purposes as this would require expensive product purification processes to remove and recover the excess for re-use. However, when an attempt was made to modify the processes of the literature so as to employ stoichiometric quantities of brominating agent, the conversion and product yields were significantly reduced. It has now been found that by removing the water from the reaction, very high conversions and yields (>95%) can be achieved when using substantially stoichiometric quantities of reactants. The water is a by-product of the reaction and is also present when aqueous HBr is used.

In accordance with this invention, there is provided a bromination process which comprises reacting an activated aromatic compound with HBr and a sulfoxide, while removing water from the reaction mixture, so as to ring brominate the activated aromatic compound.

THE INVENTION

The process of the invention can brominate activated aromatic compounds in high conversions and yields. By "activated aromatic compounds" is meant mono, di and multicyclic aromatic compounds, including heterocyclic compounds, which are at least moderately activated for electrophilic ring substitution by having one or more ring activating electron donating groups such as, for example, —OH, —OR, —$NH_2$, —NHR, —$NR_2$, —NHCOR, —SR and —SOR, where R in each case is hydrocarbyl or substituted hydrocarbyl having from 1 to 30 or more carbons. The aromatic compounds can contain other substituents which do not interfere with the bromination reaction.

Non-limiting examples of sulfoxides which are suitable for use in the process of the invention include alkyl, cycloalkyl and aryl sulfoxides such as dimethyl sulfoxide, diethyl sulfoxide, di-n-propyl sulfoxide, di-n-butyl sulfoxide, tetramethylene sulfoxide, diphenyl sulfoxide and the like. Preferred is dimethyl sulfoxide (DMSO).

Aqueous HBr, for example about 40 to 60 wt % HBr, is conveniently used, although anhydrous HBr can be bubbled into an inert solvent which contains the sulfoxide and the aromatic compound. The sulfoxide/HBr brominating agent can also be pre-formed and then mixed with the aromatic compound. In fact, the reactants can be added in any order. Although the process does not require the use of any added solvent, it is preferred to carry out the reaction in an inert solvent which contains the sulfoxide and the aromatic compound. The HBr is then gradually added to the reaction so as to avoid the formation of a solid bromide salt when brominating compounds such as amines.

Suitable inert solvents include inert organic hydrocarbyl and halogenated hydrocarbyl solvents such as, for example, benzene, toluene, xylene, chlorobenzene, cyclohexane, ethylene dichloride and the like. Preferably, amounts of solvent of from about 10 to 90 weight percent of the reaction mixture are used.

By removing the water from the reaction, including both water which is added to the reaction by the use of aqueous HBr and the water which is formed in the reaction, high conversions and yields (>95%) can be obtained, even when using substantially stoichiometric amounts of reactants. By "substantially stoichiometric amounts" is meant from about equivalent molar amounts of aromatic compound, sulfoxide and HBr up to about a 15% excess of sulfoxide and/or HBr over the equivalent molar amount. Preferably, for economic reasons, any excess, and especially excess sulfoxide, should be kept to no more than about 5%. Although monobrominated products are normally desired, such that about a 1:1:1 molar ratio of reactants represents a stoichiometric amount, when the activated aromatic compound is expected to substitute two or more bromine atoms, then the mole ratios are adjusted accordingly so as to provide the required stoichiometric amount of brominating agent.

Preferred reaction temperatures usually range from about 50° to 150° C. or higher, depending upon the boiling point of the solvent, although any temperature which is effective to provide good conversions and yields of product can be used. Subatmospheric pressures can be employed to facilitate the removal of water from the reaction mixture. Although any convenient procedure can be employed to remove water from the reaction, a preferred way is to remove it as an azeotrope along with some of the solvent. The water is collected by any standard means such as, for example, a Dean-Stark trap. The solvent portion is returned to the reaction. If a reaction solvent is not used, then the water is simply distilled from the reaction mixture. By-product organic sulfide is also allowed to escape from the reaction mixture and is collected, such as by the use of a cold trap. After the reaction is completed, any remaining acid is neutralized such as by washing with aqueous base. When a reaction solvent is used, the product is recovered by stripping the solvent. By removing the water from the reaction, conversions of >99% and yields of about 98% can be obtained when using substantially stoichiometric amounts of reactants. In contrast, the processes reported in the literature use large excesses of sulfoxide and/or HBr to obtain comparable conversions and yields.

EXAMPLES

The process is further illustrated by, but is not intended to be limited to, the following examples. Commercially available 2,6-diisopropylaniline (DIPA) contains small amounts (~5 wt %) of various other isomers. The conversions and yields stated are the sum of all of the isomers and are reported as gas chromatograph area percents (GC area %). In all experiments, the by-product dimethyl sulfide was allowed to escape from the reaction vessel.

Example 1

To a 1 liter round bottom flask equipped with a magnetic stirrer are fed commercially available 2,6-diisopropylaniline (200.0 g, 1.13 mole, ~95 wt % 2,6-diisopropylaniline), toluene (200.0 g) and dimethyl sulfoxide (90.0 g, 1.15 mole). This solution is heated to ~90° C. and 48 wt % aqueous HBr (200.0 g, 1.19 mole) is added through an addition funnel with stirring while removing the water azeotropically (84° C.) using a Dean-Stark trap. The toluene is returned to the reaction mixture and the dimethyl sulfide is allowed to escape to a cold trap. After all the water is removed, the temperature is raised to 110° C. (reflux) and heating is continued for ~2 hours. At this point, the conversion is >99% and the yield of monobrominated (BDIPA-predominately 4-bromo) product is 98% (G.C. area %). The product contains ~93% of the 2,6-diisopropyl-4-bromoaniline isomer with the remainder being the brominated products of the other DIPA isomers which are contained in the starting material. The toluene solution is washed with dilute aqueous (10 wt %) caustic and the toluene is stripped to give the product.

Example 2

2,6-Diisopropylaniline (5.0 g, 28.2 mmol), DMSO (2.3 g, 29.5 mmol), 48% aqueous HBr (5.3 g, 31.4 mmol) and xylenes (15.0 g) are placed in a 50 mL flask and the mixture is heated with stirring to 70° C. for 1 hour at which time the conversion is 74%. The temperature is raised so as to azeotropically remove the water and after 1 hour the conversion is 91% and the yield of BDIPA product is 90%.

Example 3

Forty-eight percent aqueous HBr (100.1 g, 593 mmol) is added through an addition funnel over 10 minutes to a stirred solution of 2,6-diisopropylaniline (100.0 g, 565 mmol) and DMSO (45.2 g, 579 mmol) in toluene (100.3 g) at 90° C. The water is azeotropically removed. After 3 hours the conversion is 75%. The mixture is then heated to 100° C. for an additional 15 hours after which the conversion is 99.9% and the yield of BDIPA product is 98.8%.

Example 4

Forty-eight percent aqueous HBr (500.0 g, 2.96 mol) is slowly added through an addition funnel to a stirred solution of 2,6-diisopropylaniline (500.0 g, 2.82 mol) and DMSO (225.1 g, 2.89 mol) in toluene (500.0 g) in a 3 liter flask over 1.5 hour at 95° C. while azeotropically removing the water. One hour after completing the HBr addition, the conversion is 85% and after an additional 1.5 hour, the conversion is 95.5% and the yield of BDIPA product is 95.2%.

Example 5

Forty-eight percent aqueous HBr (150 g, 889 mmol) is slowly added to a mixture of 2,6-diisopropylaniline (150 g, 847 mmol) and DMSO (67.8 g, 869 mmol) at 100° C. over 2.25 hours with the water being distilled off. After the addition is completed, the heating was continued for 2.5 hour after which the conversion is 97% and the yield of BDIPA is 96%.

Comparison 1

A DIPA-HBr salt (5.0 g, 19.4 mmol) and DMSO (1.6 g, 20.5 mmol) in toluene (10.0 g) is heated to 70° C. for 18 hours with stirring during which time the mixture turns deep purple and the conversion is only 79%. Sixty percent aqueous HBr (0.65 g, 4.8 mmol) is then added and after 1 hour, the conversion is 96% and the yield of BDIPA product is 94.8%.

Comparison 2

2,6-Diisopropylaniline (100.0 g, 565 mmol) is added dropwise through an addition funnel to a mixture of toluene (300 mL) and 60 wt % aqueous HBr (88.4 g, 655 mmol) with mechanical stirring at 65° C. After the addition, the slurry is stirred at 65° C. for 1 hour, then heated to 85° C. DMSO (51.0 g, 654 mmol) is added dropwise over 45 minutes. Fifteen minutes after the addition, the conversion is 47%. Heating is continued to give 59% conversion after 2 hours and 63% conversion after 3 hours. Sixty percent aqueous HBr (40 g, 296 mmol) and DMSO (21 g, 269 mmol) are then added and after one additional hour the conversion is 90%.

Comparison 3

DIPA-HBr salt (5.0 g, 19.4 mmol) in DMSO (10.0 g, 128 mmol) is heated to 115° C. for 170 minutes at which time the conversion of DIPA to BDIPA is 80%. Sixty percent aqueous HBr (1.1 g, 8.1 mmol) is added and after 20 minutes the conversion is 99% and the yield is 98.5%.

Comparison 4

DIPA-HBr salt (10.0 g, 38.8 mmol) in DMSO (10.0 g, 128 mmol) is heated to 75° C. for 1 hour at which time the conversion is only about 40%. Sixty percent aqueous HBr (4.1 g, 30 mmol) is added and heating is continued for 1 hour at which time the conversion is 99.2% and the yield is 98.9%. The reaction is quenched with aqueous $Na_2CO_3$, extracted with ether (35 g) and washed with water. The ether is stripped in vacuo to give BDIPA as a dark brown liquid (8.5 g, 86%).

Example 6

Phenol (5.0 g, 53.2 mmol) and DMSO (4.3 g, 55.1 mmol) in toluene (8.5 g) were heated to 80–85° C. Forty-eight weight percent HBr (9.4 g, 55.6 mmol) was dripped in over 2 minutes. After 1 hour, the temperature was raised to 90° C. and the water was removed azeotropically. The conversion and yields after the listed reaction times are given below.

| Time | 5 min. | 90 min. | 120 min. |
| --- | --- | --- | --- |
| Conversion | 50.7% | 91.3% | 99.9% |
| 2-Bromophenol | 10.5% | 22.6% | 24.9% |
| 4-Bromophenol | 40.1% | 68.0% | 72.4% |
| 2,4-Dibromophenol | — | 0.6% | 2.4% |

Comparison 5

The same reaction as in Example 6 was done without removing the water and maintaining the reaction at reflux (~80° C.). The conversion and yields after the listed reaction times are given below.

| Time | 5 min. | 90 min. | 120 min. | 1000 min. |
| --- | --- | --- | --- | --- |
| Conversion | 56.7% | 74.8% | 76.6% | 87.6% |
| 2-Bromophenol | 15.6% | 19.9% | 20.8% | 24.9% |
| 4-Bromophenol | 40.9% | 54.4% | 55.3% | 61.4% |
| 2,4-Dibromophenol | 0.1% | 0.3% | 0.4% | 1.2% |

The above examples and comparisons show that in the absence of water removal a large excess of HBr and/or DMSO is required in order to achieve bromination of the aromatic ring in conversions and yields of 90% or more. In contrast, water removal during the reaction as per the process of the invention provides yields of 90% or more when using substantially stoichiometric amounts of reactants. This avoids the expense of using excess brominating agent.

What is claimed is:

1. A bromination process which comprises reacting an activated aromatic compound with HBr and a sulfoxide, while removing water from the reaction mixture, so as to ring brominate said activated aromatic compound.

2. The process of claim 1 wherein the reaction is carried out in an inert organic solvent and the reaction conditions of temperature and pressure cause the water to be vaporized from the reaction mixture.

3. The process of claim 2 wherein said activated aromatic compound, HBr and sulfoxide are used in substantially stoichiometric proportions.

4. The process of claim 3 wherein said sulfoxide and HBr are each present in no greater than about a 15% excess over a molar amount which is stoichiometrically equivalent to said activated aromatic compound.

5. The process of claim 4 wherein said sulfoxide is present in no greater than about a 5% excess.

6. The process of claim 5 wherein said sulfoxide is an alkyl sulfoxide and said activated aromatic compound contains a ring activating group selected from the group consisting of —OH, —OR, —NH$_2$, —NHR, NR$_2$, NHCOR, —SR and —SOR where R in each instance is hydrocarbyl or substituted hydrocarbyl having from 1 to about 30 carbon atoms.

7. The process of claim 6 wherein said inert organic solvent is a hydrocarbon or a halogenated hydrocarbon and said sulfoxide is dimethyl sulfoxide.

8. The process according to claim 2 wherein water and solvent are removed as an azeotrope from the reaction mixture.

9. The process according to claim 7 wherein water and solvent are removed as an azeotrope from the reaction mixture.

10. The process according to claim 7 wherein said activated aromatic compound is 2,6-diisopropylaniline and the product is 2,6-diisopropyl-4-bromoaniline.

* * * * *